(12) United States Patent
Levin

(10) Patent No.: US 7,967,814 B2
(45) Date of Patent: Jun. 28, 2011

(54) CRYOPROBE WITH VIBRATING MECHANISM

(75) Inventor: Alexander Levin, Binyamina (IL)

(73) Assignee: IceCure Medical Ltd., Caesarea (IL)

( * ) Notice: Subject to any disclaimer, the term of this patent is extended or adjusted under 35 U.S.C. 154(b) by 0 days.

(21) Appl. No.: 12/700,761

(22) Filed: Feb. 5, 2010

(65) Prior Publication Data

US 2010/0198206 A1   Aug. 5, 2010

Related U.S. Application Data

(60) Provisional application No. 61/150,025, filed on Feb. 5, 2009.

(51) Int. Cl.
*A61B 18/02* (2006.01)

(52) U.S. Cl. ........................................ 606/21

(58) Field of Classification Search .............. 606/20–26
See application file for complete search history.

(56) References Cited

U.S. PATENT DOCUMENTS

| | | |
|---|---|---|
| 3,234,746 A | 2/1966 | Smith |
| 3,358,472 A | 12/1967 | Kipling |
| 3,664,344 A | 5/1972 | Bryne |
| 3,699,775 A | 10/1972 | Cowans |
| 3,712,306 A | 1/1973 | Bryne |
| 3,736,936 A | 6/1973 | Basiulis |
| 3,800,552 A | 4/1974 | Sollami |
| 3,862,630 A | 1/1975 | Balamuth |
| 3,882,849 A | 5/1975 | Jamshidi |
| 3,938,505 A | 2/1976 | Jamshidi |
| 3,971,383 A | 7/1976 | Van Gerven |
| 4,082,096 A | 4/1978 | Benson |
| 4,091,634 A | 5/1978 | Shepherd |
| 4,127,903 A | 12/1978 | Schachar |
| 4,200,104 A | 4/1980 | Harris |
| 4,211,231 A | 7/1980 | Rzasa |
| 4,279,626 A | 7/1981 | Buchmuller |
| 4,306,568 A | 12/1981 | Torre |
| 4,313,306 A | 2/1982 | Torre |

(Continued)

FOREIGN PATENT DOCUMENTS

CA   2437079   6/2004

(Continued)

OTHER PUBLICATIONS

Verkin et al., Low Temperatures in Stomatology, Naukova Dumka, 1990, pp. 62-63, Kiev.

(Continued)

*Primary Examiner* — Michael Peffley
*Assistant Examiner* — Benjamin Lee
(74) *Attorney, Agent, or Firm* — The Law Offices of Michael E. Kondoudis

(57) ABSTRACT

Cryoprobes and a cryotherapy method. A cryoprobe includes: a shaft having a central axis, a tip at a first end, a male socket section at a second end opposite the first end, a cryogen feeding pipe extending from the tip through the male socket section along the axis, and a cryogen return passage extending from the tip through the male socket section; and a handle having a female socket adapted and configured to receive and connect with the male socket section in a quick connect manner, a vibration section that selectively causes vibration along the axis, a cryogen exhaust passage extending from the female socket to an exterior of the handle, and a cryogen supply tube connected to the female socket at an end of the tube.

19 Claims, 5 Drawing Sheets

U.S. PATENT DOCUMENTS

| | | | |
|---|---|---|---|
| 4,367,744 A | 1/1983 | Sole | |
| 4,428,748 A | 1/1984 | Peyman | |
| 4,463,458 A | 8/1984 | Seidner | |
| 4,481,948 A | 11/1984 | Sole | |
| 4,487,253 A | 12/1984 | Malek | |
| 4,552,208 A | 11/1985 | Sorensen | |
| 4,570,626 A | 2/1986 | Norris | |
| 4,573,525 A | 3/1986 | Boyd | |
| 4,611,654 A | 9/1986 | Buchsel | |
| 4,617,018 A | 10/1986 | Nishi | |
| 4,676,225 A | 6/1987 | Bartera | |
| 4,724,834 A * | 2/1988 | Alperovich et al. | 606/23 |
| 4,726,194 A | 2/1988 | Mackay et al. | |
| 4,765,396 A | 8/1988 | Seidenberg | |
| 4,770,171 A | 9/1988 | Sweren | |
| 4,802,475 A | 2/1989 | Weshahy | |
| 4,823,790 A * | 4/1989 | Alperovich et al. | 606/24 |
| 4,831,856 A | 5/1989 | Gano | |
| 4,832,022 A * | 5/1989 | Tjulkov et al. | 606/22 |
| 4,946,460 A | 8/1990 | Merry et al. | |
| 5,026,387 A | 6/1991 | Thomas | |
| 5,047,043 A | 9/1991 | Kubota | |
| 5,108,390 A | 4/1992 | Potocky | |
| 5,147,355 A | 9/1992 | Friedman | |
| 5,188,102 A | 2/1993 | Idemoto | |
| 5,214,925 A | 6/1993 | Hoy | |
| 5,222,937 A | 6/1993 | Kagawa | |
| 5,224,943 A | 7/1993 | Goddard | |
| 5,243,826 A | 9/1993 | Longsworth | |
| 5,254,082 A | 10/1993 | Takase | |
| 5,254,116 A | 10/1993 | Baust | |
| 5,261,923 A | 11/1993 | Soares | |
| 5,263,957 A | 11/1993 | Davison | |
| 5,264,116 A | 11/1993 | Apelian | |
| 5,275,595 A | 1/1994 | Dobak | |
| 5,281,215 A | 1/1994 | Milder | |
| 5,295,484 A | 3/1994 | Marcus | |
| 5,324,286 A | 6/1994 | Fowle | |
| 5,330,745 A | 7/1994 | Mcdow | |
| 5,334,181 A | 8/1994 | Rubinsky | |
| 5,342,380 A | 8/1994 | Hood | |
| 5,361,591 A | 11/1994 | Caldwell | |
| 5,391,144 A | 2/1995 | Sakurai | |
| 5,411,374 A | 5/1995 | Gram | |
| 5,417,073 A | 5/1995 | James | |
| 5,423,807 A | 6/1995 | Milder | |
| 5,429,138 A | 7/1995 | Jamshidi | |
| 5,438,837 A | 8/1995 | Caldwell | |
| 5,441,512 A | 8/1995 | Muller | |
| 5,445,462 A | 8/1995 | Johnson | |
| 5,452,582 A | 9/1995 | Longsworth | |
| 5,488,831 A | 2/1996 | Griswold | |
| 5,516,505 A | 5/1996 | Mcdow | |
| 5,520,682 A | 5/1996 | Baust | |
| 5,526,821 A | 6/1996 | Jamshidi | |
| 5,547,473 A | 8/1996 | Peyman | |
| 5,573,532 A | 11/1996 | Chang | |
| 5,600,143 A | 2/1997 | Roberts | |
| 5,647,868 A | 7/1997 | Chinn | |
| 5,654,279 A | 8/1997 | Rubinsky | |
| 5,658,276 A | 8/1997 | Griswold | |
| 5,674,218 A | 10/1997 | Rubinsky | |
| 5,683,592 A | 11/1997 | Bartholomew et al. | |
| 5,687,776 A | 11/1997 | Forgash | |
| 5,716,353 A | 2/1998 | Matsuura | |
| 5,720,743 A | 2/1998 | Bischof | |
| 5,728,130 A | 3/1998 | Ishikawa | |
| 5,735,845 A | 4/1998 | Zupkas | |
| 5,771,946 A | 6/1998 | Kooy | |
| 5,787,940 A | 8/1998 | Bonn | |
| 5,800,448 A | 9/1998 | Banko | |
| 5,800,487 A | 9/1998 | Mikus | |
| 5,814,040 A | 9/1998 | Nelson | |
| 5,868,673 A | 2/1999 | Vesely | |
| 5,885,276 A | 3/1999 | Ammar | |
| 5,899,897 A | 5/1999 | Rabin | |
| 5,906,612 A | 5/1999 | Chinn | |
| 5,906,628 A | 5/1999 | Miyawaki | |
| 5,910,104 A | 6/1999 | Dobak | |
| 5,921,982 A | 7/1999 | Lesh | |
| 5,976,092 A | 11/1999 | Chinn | |
| 5,976,505 A | 11/1999 | Henderson | |
| 5,992,158 A | 11/1999 | Goddard | |
| 6,012,453 A | 1/2000 | Tsais | |
| 6,024,750 A | 2/2000 | Mastri | |
| 6,027,499 A | 2/2000 | Johnston | |
| 6,032,068 A | 2/2000 | Daniel | |
| 6,032,675 A | 3/2000 | Rubinsky | |
| 6,035,657 A | 3/2000 | Dobak | |
| 6,036,667 A | 3/2000 | Manna | |
| 6,039,730 A | 3/2000 | Rabin | |
| 6,041,787 A | 3/2000 | Rubinsky | |
| 6,042,342 A | 3/2000 | Orian | |
| 6,053,906 A | 4/2000 | Honda | |
| 6,059,820 A | 5/2000 | Baronov | |
| 6,063,098 A | 5/2000 | Houser | |
| 6,095,149 A | 8/2000 | Sharkey | |
| 6,142,991 A | 11/2000 | Schatzberger | |
| 6,152,894 A | 11/2000 | Kubler | |
| 6,182,666 B1 | 2/2001 | Dobak | |
| 6,200,308 B1 | 3/2001 | Pope | |
| 6,206,832 B1 | 3/2001 | Downey | |
| 6,212,904 B1 | 4/2001 | Arkharov | |
| 6,216,029 B1 | 4/2001 | Paltieli | |
| 6,235,018 B1 | 5/2001 | LePivert | |
| 6,237,355 B1 | 5/2001 | Li | |
| 6,251,105 B1 | 6/2001 | Mikus | |
| 6,270,494 B1 | 8/2001 | Kovalcheck | |
| 6,280,407 B1 | 8/2001 | Manna | |
| 6,354,088 B1 | 3/2002 | Emmer | |
| 6,355,033 B1 | 3/2002 | Moorman et al. | |
| 6,358,264 B2 | 3/2002 | Banko | |
| 6,379,348 B1 | 4/2002 | Onik | |
| 6,383,180 B1 | 5/2002 | Lalonde | |
| 6,383,181 B1 | 5/2002 | Johnston | |
| 6,411,852 B1 | 6/2002 | Danek | |
| 6,413,263 B1 | 7/2002 | Lobdill | |
| 6,423,009 B1 | 7/2002 | Downey | |
| 6,432,102 B2 | 8/2002 | Joye | |
| 6,457,212 B1 | 10/2002 | Craig | |
| 6,468,268 B1 | 10/2002 | Abboud | |
| 6,468,269 B1 | 10/2002 | Korpan | |
| 6,471,217 B1 | 10/2002 | Hayfield | |
| 6,482,178 B1 | 11/2002 | Andrews | |
| 6,497,714 B1 | 12/2002 | Ishikawa | |
| 6,500,109 B2 | 12/2002 | Tokita | |
| 6,503,246 B1 | 1/2003 | Har-Shai | |
| 6,508,814 B2 | 1/2003 | Tortal | |
| 6,513,336 B2 | 2/2003 | Zurecki | |
| 6,547,784 B1 | 4/2003 | Thompson | |
| 6,551,309 B1 | 4/2003 | LePivert | |
| 6,562,030 B1 | 5/2003 | Abboud | |
| 6,565,556 B1 | 5/2003 | Korpan | |
| 6,581,390 B2 | 6/2003 | Emmer | |
| 6,582,426 B2 | 6/2003 | Moorman | |
| 6,631,615 B2 | 10/2003 | Drube | |
| 6,640,556 B2 | 11/2003 | Ursan | |
| 6,659,730 B2 | 12/2003 | Gram | |
| 6,659,956 B2 | 12/2003 | Barzell et al. | |
| 6,672,095 B1 | 1/2004 | Luo | |
| 6,678,621 B2 | 1/2004 | Wiener et al. | |
| 6,682,525 B2 | 1/2004 | Lalonde | |
| 6,698,423 B1 | 3/2004 | Honkonen | |
| 6,702,761 B1 | 3/2004 | Damadian | |
| 6,761,715 B2 | 7/2004 | Carroll | |
| 6,765,333 B1 | 7/2004 | Mariaucue | |
| 6,768,917 B1 | 7/2004 | Van Vaals | |
| 6,772,766 B2 | 8/2004 | Gallo | |
| 6,786,902 B1 | 9/2004 | Rabin | |
| 6,824,543 B2 | 11/2004 | Lentz | |
| 6,852,706 B1 | 2/2005 | Heber-Katz | |
| 6,858,025 B2 | 2/2005 | Maurice | |
| 6,869,439 B2 | 3/2005 | White | |
| 6,889,695 B2 | 5/2005 | Pankratov | |
| 6,898,940 B2 | 5/2005 | Gram | |
| 6,908,472 B2 | 6/2005 | Wiener | |
| 6,910,510 B2 | 6/2005 | Gale | |

| | | |
|---|---|---|
| 6,913,604 B2 | 7/2005 | Mihalik |
| 6,932,771 B2 | 8/2005 | Whitmore |
| 6,936,045 B2 | 8/2005 | Yu |
| 6,942,659 B2 | 9/2005 | Lehmann |
| 6,951,569 B2 | 10/2005 | Nohilly |
| 6,954,977 B2 | 10/2005 | Maguire |
| 6,995,493 B2 | 2/2006 | Isoda |
| 7,001,378 B2 | 2/2006 | Yon |
| 7,025,762 B2 | 4/2006 | Johnston |
| 7,025,767 B2 | 4/2006 | Schaefer |
| 7,071,690 B2 | 7/2006 | Butts |
| 7,081,111 B2 | 7/2006 | Svaasand |
| 7,101,367 B2 | 9/2006 | Xiao et al. |
| 7,128,739 B2 | 10/2006 | Prakash et al. |
| 7,137,978 B2 | 11/2006 | Levin |
| 7,144,228 B2 | 12/2006 | Emmer |
| 7,151,374 B2 | 12/2006 | Doty |
| 7,160,291 B2 | 1/2007 | Damasco |
| 7,160,292 B2 | 1/2007 | Moorman |
| 7,165,422 B2 | 1/2007 | Little |
| 7,189,228 B2 | 3/2007 | Eum |
| 7,207,985 B2 | 4/2007 | Duong |
| 7,213,400 B2 | 5/2007 | Dickerson |
| 7,223,080 B2 | 5/2007 | Duron |
| 7,250,046 B1 | 7/2007 | Fallat |
| 7,252,648 B2 | 8/2007 | Honda |
| 7,255,693 B1 | 8/2007 | Johnston |
| 7,273,479 B2 | 9/2007 | Littrup |
| 7,278,991 B2 | 10/2007 | Morris |
| 7,280,623 B2 | 10/2007 | Gupta |
| 7,282,919 B2 | 10/2007 | Doty |
| 7,288,089 B2 | 10/2007 | Yon |
| 7,318,327 B2 | 1/2008 | Dickerson |
| 7,344,530 B2 | 3/2008 | Bischof |
| 7,344,531 B2 | 3/2008 | Bischof |
| 7,354,434 B2 | 4/2008 | zvuloni |
| 7,361,187 B2 | 4/2008 | Duong |
| 7,381,207 B2 | 6/2008 | Duong |
| 7,425,211 B2 | 9/2008 | Levin et al. |
| 7,458,968 B2 | 12/2008 | Carroll |
| 7,481,806 B2 | 1/2009 | Levin |
| 7,485,117 B2 | 2/2009 | Damasco |
| 7,498,812 B2 | 3/2009 | Doty |
| 7,510,554 B2 | 3/2009 | Duong |
| 7,563,260 B2 | 7/2009 | Whitmore |
| 7,731,711 B2 | 6/2010 | Levin |
| 7,803,154 B2 | 9/2010 | Toubia et al. |
| 2001/0047129 A1 | 11/2001 | Hall et al. |
| 2002/0016540 A1 | 2/2002 | Mikus |
| 2002/0022832 A1 | 2/2002 | Mikus |
| 2002/0040220 A1 | 4/2002 | Zvuloni et al. |
| 2002/0042609 A1* | 4/2002 | Kelman et al. ............ 606/21 |
| 2002/0077654 A1 | 6/2002 | Javier |
| 2002/0085921 A1 | 7/2002 | Gram |
| 2002/0144509 A1 | 10/2002 | Chalk |
| 2002/0156469 A1 | 10/2002 | Yon |
| 2002/0157402 A1 | 10/2002 | Drube |
| 2002/0160640 A1 | 10/2002 | Korpan |
| 2002/0161385 A1 | 10/2002 | Wiener |
| 2003/0060762 A1 | 3/2003 | Zvuloni |
| 2003/0079480 A1 | 5/2003 | Emmer |
| 2003/0126867 A1 | 7/2003 | Drube |
| 2003/0135119 A1 | 7/2003 | Lee |
| 2003/0181897 A1 | 9/2003 | Thomas |
| 2003/0220635 A1 | 11/2003 | Knowlton |
| 2004/0024391 A1 | 2/2004 | Cytron |
| 2004/0055316 A1 | 3/2004 | Emmer et al. |
| 2004/0078033 A1 | 4/2004 | Levin |
| 2004/0215178 A1 | 10/2004 | Maurice |
| 2005/0016185 A1 | 1/2005 | Emmer |
| 2005/0038422 A1 | 2/2005 | Maurice |
| 2005/0056027 A1 | 3/2005 | White |
| 2005/0086949 A1 | 4/2005 | Noble |
| 2005/0106153 A1 | 5/2005 | Nordouist |
| 2005/0177147 A1 | 8/2005 | Vancelette |
| 2005/0192564 A1 | 9/2005 | Cosman et al. |
| 2005/0214268 A1 | 9/2005 | Cavanagh |
| 2005/0274142 A1 | 12/2005 | Corey |
| 2006/0049274 A1 | 3/2006 | Hume |
| 2006/0053165 A1 | 3/2006 | Hume |
| 2006/0079867 A1 | 4/2006 | Berzak |
| 2006/0122590 A1 | 6/2006 | Bliweis |
| 2006/0155267 A1 | 7/2006 | Berzak |
| 2006/0155268 A1 | 7/2006 | Amir |
| 2006/0264920 A1 | 11/2006 | Duong |
| 2006/0293647 A1 | 12/2006 | McRae |
| 2007/0000259 A1 | 1/2007 | Brook |
| 2007/0043342 A1* | 2/2007 | Kleinberger ............ 606/21 |
| 2007/0088217 A1* | 4/2007 | Babaev ............ 600/471 |
| 2007/0093710 A1 | 4/2007 | Maschke |
| 2007/0129626 A1 | 6/2007 | Mahesh |
| 2007/0129629 A1 | 6/2007 | Beauregard |
| 2007/0149959 A1 | 6/2007 | DeLonzor |
| 2007/0166171 A1 | 7/2007 | Kondo |
| 2007/0167939 A1 | 7/2007 | Duong |
| 2007/0276360 A1 | 11/2007 | Johnston |
| 2008/0027419 A1 | 1/2008 | Hamel |
| 2008/0039745 A1* | 2/2008 | Babaev ............ 601/2 |
| 2008/0051774 A1 | 2/2008 | Ofir |
| 2008/0051776 A1 | 2/2008 | Bliweis |
| 2008/0097251 A1* | 4/2008 | Babaev ............ 601/2 |
| 2008/0115509 A1 | 5/2008 | Gullickson |
| 2008/0119834 A1 | 5/2008 | Vancelette |
| 2008/0119838 A1 | 5/2008 | Vancelette |
| 2008/0319433 A1 | 12/2008 | Geiselhart |
| 2009/0011032 A1 | 1/2009 | LePivert |

FOREIGN PATENT DOCUMENTS

| | | |
|---|---|---|
| DE | 202004008875 U1 | 8/2004 |
| DE | 102005050344 | 5/2007 |
| EP | 0292922 B1 | 11/1988 |
| EP | 395307 A2 | 10/1990 |
| EP | 570301 | 11/1993 |
| EP | 955012 | 11/1999 |
| EP | 919197 B1 | 2/2005 |
| GB | 1108905 | 4/1968 |
| GB | 1402737 | 8/1975 |
| GB | 1473856 | 5/1977 |
| GB | 1534472 | 12/1978 |
| GB | 2336781 | 11/1999 |
| GB | 2409815 A1 | 7/2005 |
| JP | 2004041428 A2 | 2/2004 |
| JP | 2007144180 A2 | 6/2007 |
| JP | 2007167100 | 7/2007 |
| WO | WO8303961 A1 | 11/1983 |
| WO | WO9637158 A1 | 11/1996 |
| WO | WO9639960 A1 | 12/1996 |
| WO | WO9947876 A1 | 9/1999 |
| WO | WO0137919 A2 | 5/2001 |
| WO | WO0141683 A2 | 6/2001 |
| WO | WO0189183 A1 | 11/2001 |
| WO | WO0197702 | 12/2001 |
| WO | WO0202026 A1 | 1/2002 |
| WO | WO03015651 A1 | 2/2003 |
| WO | WO2004060465 | 7/2004 |
| WO | WO2004051409 A2 | 8/2004 |
| WO | WO2004093635 A2 | 11/2004 |
| WO | WO2005098308 A1 | 10/2005 |
| WO | WO2005000106 A2 | 12/2005 |
| WO | WO2006116457 A2 | 11/2006 |
| WO | WO2006127467 | 11/2006 |
| WO | WO2007028232 A1 | 3/2007 |
| WO | WO2007086056 A2 | 8/2007 |
| WO | WO2007129308 | 11/2007 |

OTHER PUBLICATIONS

International Search Report and Written Opinion dated Nov. 5, 2008 in corresponding International Application No. PCT/IL2008/000794.

Qi et al., Development and performance test of a cryoprobe with heat transfer configuration enhancement, Cryogenics, 2006, pp. 881-887, vol. 46, Elsevier.

International Search Report dated Mar. 25, 2010 in corresponding International Application No. PCT/IB2009/052615.

International Search Report and Written Opinion dated Jul. 23, 2009 in corresponding International Application No. PCT/IL2009/000062.

International Search Report and Written Opinion dated Dec. 22, 2008 in corresponding International Application No. PCT/IL2008/001114.

International Search Report and Written Opinion dated Sep. 4, 2009 in corresponding International Application No. PCT/IB2009/051532.

Office Action dated Jan. 22, 2010 in Application No. EP 07805563.9.

International Search Report and Written Opinion dated Nov. 28, 2008 in corresponding International Application No. PCT/IL2008/000943.

International Search Report and Written Opinion dated Jan. 29, 2008 in corresponding International Application No. PCT/IL2007/001103.

International Search Report and Written Opinion dated Jan. 30, 2008 in corresponding International Application No. PCT/IL2007/001142.

International Search Report and Written Opinion dated Nov. 6, 2007 in corresponding International Application No. PCT/IL2007/000974.

Qi et al., Flow boiling of liquid nitrogen in micro-tubes: Part I—onset of nucleate boiling, two phase flow instability and two phase flow drop, International Journal of Heat and Mass Transfer, 2007, pp. 4999-5016, vol. 50, Elsevier.

Qi et al., Flow boiling of liquid nitrogen in micro-tubes: Part II—heat transfer characteristics and critical heat flux, International Journal of Heat and Mass Transfer, 2007, pp. 5017-5030, vol. 50, Elsevier.

Zhang et al., Two phase flow characteristics of liquid nitrogen in vertically upward 0.5 and 1.0 mm micro-tubes: Visualization studies, Cryogenics, 2009, pp. 565-575, vol. 49, Elsevier.

International Search Report and Written Opinion dated Aug. 24, 2010 in corresponding International Application PCT/US2010/34467.

U.S. Appl. No. 12/360,221, filed Jan. 27, 2009, Levin, Arbel Medical Ltd.

U.S. Appl. No. 11/851,055, filed Sep. 6, 2007, Toubia et al., Arbel Medical Ltd.

U.S. Appl. No. 12/017,035, filed Jan. 20, 2008, Toubia et al., Arbel Medical Ltd.

U.S. Appl. No. 11/763,093, filed Jun. 14, 2007, Levin et al., Arbel Medical Ltd.

U.S. Appl. No. 12/278,733, filed Nov. 5, 2008, Levin et al., Arbel Medical Ltd.

U.S. Appl. No. 11/857,085, filed Sep. 18, 2007, Levin et al., Arbel Medical Ltd.

U.S. Appl. No. 12/668,428, filed Sep. 7, 2010, Levin et al.

U.S. Appl. No. 12/673,506, filed Feb. 15, 2010, Levin et al.

U.S. Appl. No. 12/237,805, filed Sep. 25, 2008, Levin et al., Arbel Medical Ltd.

U.S. Appl. No. 12/313,611, filed Nov. 21, 2008, Toubia et al., Arbel Medical Ltd.

U.S. Appl. No. 12/812,819, filed Sep. 29, 2010, Toubia et al., IceCure Medical Ltd.

U.S. Appl. No. 12/988,233, filed Oct. 15, 2010, Toubia et al., Arbel Medical Ltd.

U.S. Appl. No. 12/611,938, filed Nov. 4, 2009, Levin.

U.S. Appl. No. 12/731,219, filed Mar. 25, 2010, Berzak et al., IceCure Medical Ltd.

U.S. Appl. No. 12/778,172, filed May 12, 2010, Berzak et al., IceCure Medical Ltd.

U.S. Appl. No. 12/846,047, filed Jul. 29, 2010, Berzak et al., IceCure Medical Ltd.

\* cited by examiner

CRYOPROBE WITH VIBRATING MECHANISM

CROSS-REFERENCE TO RELATED APPLICATION

This application claims the benefit of priority from U.S. Provisional Application No. 61/150,025, filed on Feb. 5, 2009, which is hereby incorporated by reference as if set forth herein in full.

BACKGROUND

1. Technical Field

The present invention relates to a cryosurgical system, and in particular to a cryosurgical system that features a vibrating cryoprobe.

2. Description of Background Art

In cryosurgery, penetration of a cryoprobe into a dense tumor can be a primary challenge. Several approaches to meet this challenge are known.

For example, U.S. Patent Publication No. 20070149959 "Cryoprobe for low pressure systems" describes a cryoprobe with a pointed distal penetrating segment, which makes penetration into a tumor significantly easier. However, such cryoprobe has a significant drawback: it is too traumatic for any non-target tissue situated behind the target tumor, which is also likely to be damaged during treatment of the tumor.

Apart from cryotherapy, other patents describe the application of vibrations to other types of surgical instruments with concomitant easier penetration into living tissue.

U.S. Pat. No. 7,252,648 "Ultrasound puncture system" describes an ultrasound puncture system, which comprises a handpiece which accommodates an ultrasound vibrator, a puncturing probe for transmitting ultrasound waves to a biological wall which is to be punctured, an outer cover tube covering the probe and attached to the handpiece, and an ultrasound power source unit for driving the ultrasound vibrator, wherein the ultrasound power source unit comprises a termination unit for terminating the energy supply to the ultrasound vibrator, an impedance detector for detecting the puncture state of the probe, and a fluid supply unit for supplying a fluid to the distal end opening of the outer cover tube and probe, wherein the penetration of the probe through the biological wall is detected with the detection unit and the supply of energy to the ultrasound vibrator is terminated based on the detection output.

U.S. Pat. No. 6,908,472 "Apparatus and method for altering generator functions in an ultrasonic surgical system" teaches a system for implementing surgical procedures, which includes an ultrasonic surgical hand piece having an end-effector, a console having a digital signal processor (DSP) for controlling the hand piece, an electrical connection connecting the hand piece and the console, and a memory, such as an EEPROM (Electrically Erasable Programmable Read Only Memory), disposed in the electrical connection. The console sends a drive current to drive the hand piece which imparts ultrasonic longitudinal movement to the blade. However the blade only moves through application of ultrasound.

U.S. Pat. No. 6,765,333 "Power assistance device for an ultrasonic vibration dental handpiece" describes a power assistance device for an ultrasonic dental handpiece (5), which again relies upon ultrasound.

U.S. Pat. No. 6,702,761 "Vibration assisted needle device" describes a vibration assisted needle device for use in medical procedures, such as needle aspiration biopsies. Reciprocation of the needle, such as a biopsy needle, eases the advance of the needle through tissue, penetration of the site of interest and the collection of sample at a site of interest. The device comprises a housing defining a chamber, a needle support external to the chamber for supporting a needle and a mechanism in the chamber for causing reciprocal motion of the needle support. The needle support is preferably external to the housing. A syringe support may be connected to the housing for supporting a syringe. The reciprocal mechanism may comprise means for converting rotational motion into reciprocating motion, such as a bearing or a rotor with a circumferential, angled groove on its surface, coupled to the needle support. The bearing or the rotor may be driven by a rotational motor, preferably located outside of the housing, or by a hydraulically driven turbine within the housing. Alternatively, the reciprocal mechanism means may comprise a stationary solenoid and a movable solenoid for being coupled to the needle. Preferably, a second stationary solenoid is provided and the moving solenoid is between the two stationary solenoids. Energization of the stationary solenoid or solenoids by an alternating current, for example, and energization of the movable solenoid by a direct current, or vice a versa, attracts and repulses the movable solenoid, causing reciprocal of the needle. Methods and systems using the vibration assisted needle device are also disclosed. However, only the needle is provided for treatment, without any other type of treatment.

U.S. Pat. No. 6,497,714 "Ultrasonic trocar" describes a trocar having a needle unit. The needle unit has a paracentric section, which is substantially pyramidal. The paracentric section has two curved surfaces that diagonally oppose each other. The surfaces are formed by cutting the ridges of the section, which diagonally oppose each other. The remaining two ridges of the paracentric section make, respectively, sharp cutting edges for cutting living tissues. The cutting edges are substantially symmetrical to each other with respect to the axis of the needle unit. However, this device is only operative with a trocar for deep surgical (cutting) procedures.

U.S. Pat. No. 6,053,906 "Ultrasonic operation apparatus" teaches a control unit, which comprises a load state detector for detecting a load state of a load acting on a treatment section when the treatment section is put in contact with a living tissue, and a bar-graph display for indicating the load state in relation to ultrasonic oscillation on the basis of a detection result from the load state detector; again it only operates on the basis of ultrasound.

U.S. Pat. No. 5,728,130 "Ultrasonic trocar system" describes an ultrasonic trocar system, which includes a cannula having a guide bore, an obturator to be passed through the guide bore of the cannula so that the obturator can be removed, and a vibration generator for generating ultrasonic vibrations to be propagated to the obturator. The obturator is vibrated at an ultrasonic frequency to puncture a somatic layer. An intermediate member is interposed between the cannula and obturator. Again this device relies upon ultrasound.

Another challenge, which is related to the operation characteristics of cryosurgical probes, is achieving sufficiently large ice-ball in the freezing process and, therefore—achieving sufficiently large necrosis zone of the target tissue. However, there are currently no solutions available that provide both good penetration to dense tissue and also provide a sufficiently large ice-ball during the freezing process.

BRIEF SUMMARY

Absent from the background art is a cryoprobe that features vibrations in the axial direction.

The present invention satisfies this absence by providing a vibrating cryoprobe for easier and/or more effective penetration into tissue, for example and without limitation, optionally for easier and/or more effective penetration into dense tumors. In addition, without wishing to be limited by a single hypothesis, it is believed that vibration of the cryotip of the cryoprobe in the process of its freezing operation can facilitate formation of an ice-ball surrounding the cryotip and thereby may enlarge the zone of necrosis in the target tissue.

It is known that vibration of the heat transferring surface can significantly facilitate the process of heat transfer (see, for example: Pak H. Y. et al. CONVECTION HEAT TRANSFER IN A CONTAINED FLUID SUBJECTED TO VIBRATION, IN "AUGMENTATION OF HEAT TRANSFER", pp. 148-157, ASME, New-York, 1970). In such a way, a proper technique of cryotip vibration may significantly improve surgical characteristics of a cryoprobe with a certain diameter. However, the background art never considered application of vibrations to the operation of any type of cryogenic device.

One aspect of the present invention provides a cryoprobe comprising: a shaft having a central axis, a tip at a first end, a male socket section at a second end opposite the first end, a cryogen feeding pipe extending from the tip through the male socket section along the axis, and a cryogen return passage extending from the tip through the male socket section; and a handle having a female socket adapted and configured to receive and connect with the male socket section in a quick connect manner, a vibration section that selectively causes vibration along the axis, a cryogen exhaust passage extending from the female socket to an exterior of the handle, and a cryogen supply tube connected to the female socket at an end of the tube. When the male socket section is received by and connected with the female socket section, the cryogen exhaust passage is in communication with the cryogen return passage, the cryogen supply tube is in communication with the cryogen feeding pipe, and the vibration section selectively causes the male socket section to vibrate along the axis.

Another aspect of the present invention provides a cryoprobe comprising: a rigid shaft having a tip at a distal end, a male socket section at a proximal end, inner and outer passages extending from the tip through the male socket section; and a body having a female socket section that connects with the male socket section, a vibration section that selectively causes axial vibration, a cryogen exhaust passage extending from the female socket to ambient, and a cryogen supply tube connected to the female socket. When the male and female socket sections are connected, the cryogen exhaust passage is in communication with the outer passage, the cryogen supply tube is in communication with the inner passage, and the vibration section selectively causes the male socket section to vibrate axially.

Still another aspect of the present invention provides a method of cryotherapy of a subject, comprising treating a tissue of the subject with a cryoprobe having a tip, said cryoprobe providing simultaneous axial vibration of at least said tip and cryotherapy through at least said tip to said tissue.

Yet another aspect of the present invention provides a cryotherapy method, comprising: vibrating a cryotip of a cryoprobe in an axial direction; positioning the cryotip in a target tissue; and cooling the cryotip.

These, additional, and/or other aspects and/or advantages of the present invention are: set forth in the detailed description which follows; possibly inferable from the detailed description; and/or learnable by practice of the present invention.

BRIEF DESCRIPTION OF THE DRAWINGS

The present invention will be more readily understood from the detailed description of embodiments thereof made in conjunction with the accompanying drawings of which.

DETAILED DESCRIPTION

Figure 1:
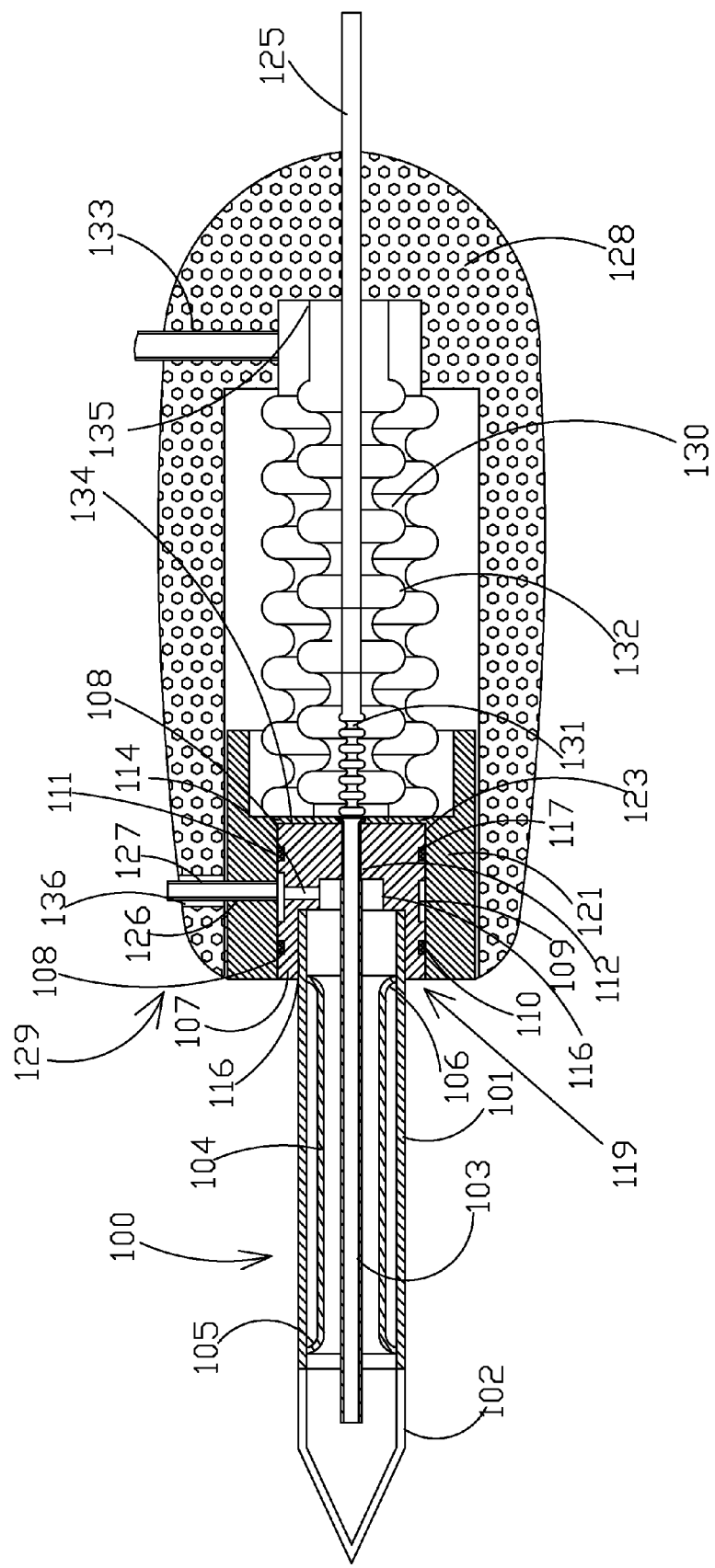
FIG. 1 is an axial cross-section of an exemplary, non-limiting, illustrative cryoprobe with a built-in vibrating pneumatic mechanism constructed from two concentric bellows, consistent with at least one embodiment of the present invention.

Reference will now be made in detail to embodiments of the present invention, examples of which are illustrated in the accompanying drawings, wherein like reference numerals refer to the like elements throughout. The embodiments are described below to explain the present invention by referring to the figures.

FIG. 1 is an axial cross-section of an exemplary, non-limiting, illustrative cryoprobe with its proximal male and female quick coupling units, a handle with a built-in vibrating pneumatic mechanism constructed from two concentric bellows, consistent with at least one embodiment of the present invention.

This embodiment of cryoprobe 100 comprises a shaft 101 and a handle 128.

The shaft 101 includes a cryotip 102 at a distal end. Shaft 101 is preferably fabricated from a rigid material. A central cryogen feeding pipe 103 is situated in shaft 101, along a central axis thereof. The central feeding pipe 103 includes a distal end that terminates in the cryotip 102 and a proximal end that protrudes at least partially from the proximal end of shaft 101. The very proximal end of the central feeding pipe 103 is turned-along or grooved. The proximal sections of shaft 101 and the central feeding pipe 103 serve for installation of a male unit 119 of a quick coupling mechanism as described herein.

Thermal insulation of shaft 101 is preferably provided by an intermediate tube 104 with two flanged ends 101 and 106, wherein the outer diameter of the formed flanges 105 and 106 conforms to the internal diameter of the shaft 101. Friction between the internal surface of shaft 101 and flanged end 106 ensures stable positioning of the intermediate tube 104 with regard to shaft 101.

The male unit 119 of the quick coupling mechanism comprises a male socket section, which is installed on the proximal sections of shaft 101 and the central feeding pipe 103; the male socket section preferably comprises bushing 107; the outer and internal surfaces of this bushing 107 are preferably stepped.

The outer surface of bushing 107 preferably comprises proximal and distal cylindrical sections 108 and a middle section 109; the proximal and distal sections 108 preferably have the same diameter, while the diameter of the middle section 109 is preferably somewhat smaller. The proximal and distal cylindrical sections 108 are preferably provided with annular grooves 111 and 110 for installation of preferably cryogenically stable polymer o-rings 120 and 117.

The inner surface of bushing 107 is preferably also stepped and preferably has distal, intermediate and proximal sections 116, 115 and 112 with progressively decreasing diameters.

Bushing 107 is installed on the proximal sections of shaft 101 and the central feeding pipe 103 such that the distal section 116 of the inner surface of the bushing 107 is fitted tightly on the proximal section of the shaft 101 and the proximal section 112 of the inner surface of bushing 107 is fitted slidingly on the turned-along or grooved proximal section of the central feeding pipe 103. After positioning bushing 107 on the proximal section of shaft 101, the proximal edge of the central feeding pipe 103 is flanged for sealing the gap between the proximal section 112 of the internal surface of bushing 107 and the central feeding pipe 103. Preferably a first through channel 114 communicates between the internal and external spaces of bushing 107 at the inner intermediate section 115 and the outer middle section 109.

The handle 128 includes a female socket section that receives the male socket section. The female unit 129 of the quick coupling mechanism comprises the female socket section and includes a housing 121 having cylindrical inner cavity 123, wherein the diameter of the cylindrical inner cavity 123 of the inner cavity conforms to the outer diameter of the distal and proximal sections 108 of the outer surface of bushing 107.

A through opening 122 in the proximal face plane of the cylindrical inner cavity 123 features a cryogen supply tube 125 supplying the cryogen into cryoprobe 100. The distal section of cryogen supply tube 125 is provided with a bellows 131 for a spring-actuated join between the central feeding pipe 103 and the cryogen supply tube 125. The tolerances of the bushing 107 and the housing 121 preferably permit sliding insertion of bushing 107 of cryoprobe 100 into housing 121 of the female unit 129; polymer o-rings 120 and 117 installed in the aforementioned annular grooves 110 and 111 of bushing 107 ensure required sealing.

There is a second through channel 126 with an outlet connection 127 installed on the outer end of the second through channel 126, which communicates with the annular channel formed between the middle section 109 of bushing 107 and the outer area of housing 121. An opening 136 in handle 128 communicates with outlet connection 127. Diameter of opening 136 is preferably significantly larger than the outer diameter of the outlet connection 127, such that opening 136 does not prevent vibration of outlet connection 127 together with cryoprobe 100 in the axial direction.

In such a way, first through channel 114, the annular channel and second through channel 126 enable the evaporated cryogen to be exhausted from cryoprobe 100.

There is preferably a plurality of concentric bellows, shown as two concentric bellows 130 and 132, as a non-limiting example, situated around the distal and middle sections of the cryogen supply tube 125. These bellows 130 and 132 are sealed at their distal and proximal ends by members 134 and 135. The internal space between the bellows 130 and 132 is preferably in fluid communication with a source of high air pressure and low air pressure via an inlet-outlet connection 133 (not shown). The quick coupling female unit 129 and bellows 132 and 130 are preferably installed in handle 128.

Oscillating change of pressure in the internal space between the bellows 130 and 132 causes vibration of member 134 in the axial direction and, in turn, vibration of cryoprobe 100 in the axial direction as well.

A preferred frequency of vibration is in the range of tens up to hundreds Hz. This axial vibration facilitates penetration process of the cryoprobe into tissue of a patient, when the cryoprobe is in its warm state before execution of freezing process.

In operation, cryogen enters central feeding pipe 103 in shaft 101 and travels to cryotip 102, thereby cooling the temperature of cryotip 102 to enable freezing of tissue surrounding cryotip 102 (not shown) and preferably formation of an iceball. Simultaneously, axial vibrations of at least cryotip 102 are provided by an oscillating change of pressure in the internal space between the bellows 130 and 132, through alternating entry of air from a source of high air pressure and low air pressure via inlet-outlet connection 133. Such an oscillating change of pressure causes vibration of member 134 in the axial direction and, in turn, vibration of at least cryotip 102 and preferably cryoprobe 100 in the axial direction as well. Stated another way, when the male socket section is received by the female socket in a quick connect manner, the cryogen exhaust passage is in communication with the cryogen return passage, the cryogen supply tube is in communication with the cryogen feeding pipe, and the vibration section selectively causes the male socket section to vibrate along the axis.

Other non-limiting, exemplary embodiments of this invention also provide easier penetration to dense tissue.

Figure 2:
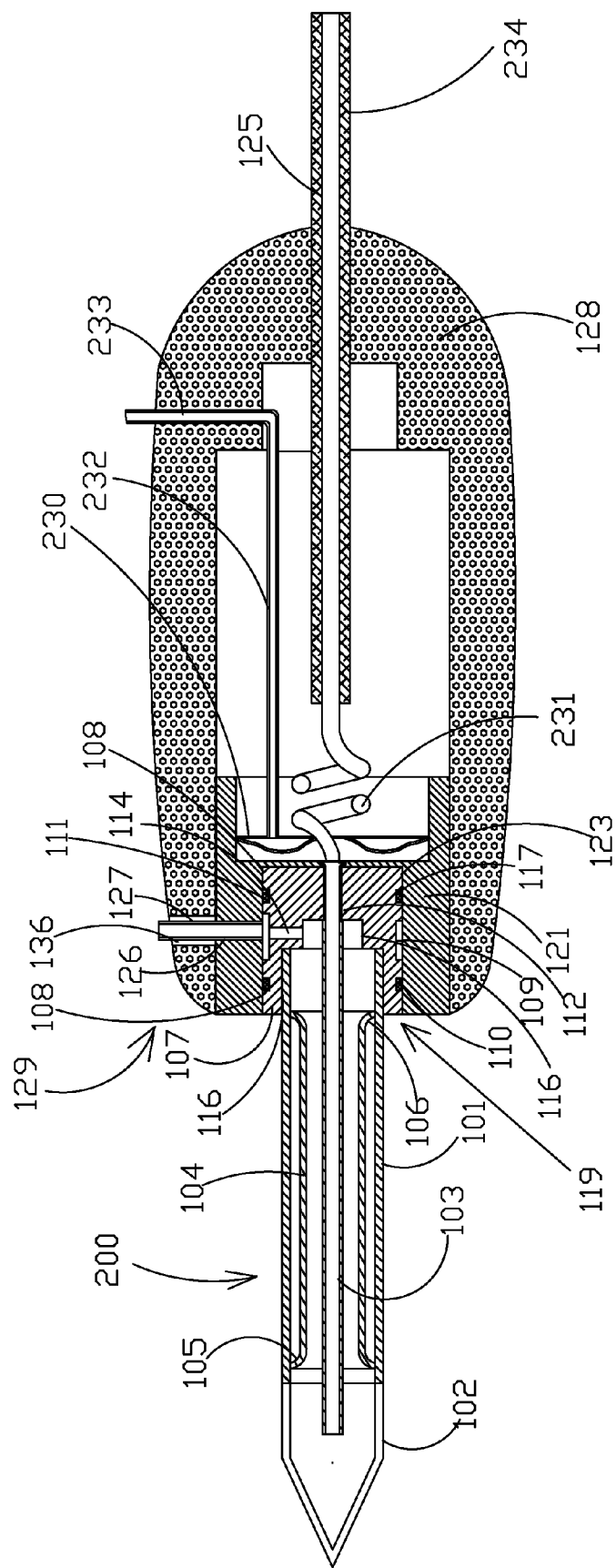
FIG. 2 is an axial cross-section of an exemplary, non-limiting, illustrative cryoprobe with a built-in vibrating pneumatic mechanism constructed from a diaphragm, consistent with at least one embodiment of the present invention.

Referring now to FIG. 2, there is illustrated an axial cross-section of an exemplary, non-limiting, illustrative cryoprobe with its proximal male and female quick coupling units, a handle with a built-in vibrating pneumatic mechanism constructed from a flat bellows, consistent with at least one embodiment of the present invention.

In FIG. 2, like numerals are used to identify like elements of cryoprobe 200 that have the same or similar function as the cryoprobe 100 of FIG. 1.

The distal section of the cryogen supply tube 125 is preferably shaped as a helical coil 231, and the proximal section of the cryogen supply tube 125 is preferably provided with a thermal insulation 234.

A diaphragm 230 is positioned concentrically around the distal section of the cryogen supply tube 125 and in immediate contact with the female quick coupling unit 129.

This diaphragm 230 is preferably in fluid communication with a source of high air pressure and low air pressure (not shown) via an inlet-outlet connection 233.

In operation, cryogen again preferably enters as described for cryoprobe 100 of FIG. 1. For the application of simultaneous axial vibrations, diaphragm 230 oscillates through alternating entry of air from the source of high air pressure and low air pressure via inlet-outlet connection 233. The oscillation of diaphragm 230 then causes helical coil 231 to oscillate and hence axial vibrations of at least cryotip 102 and preferably cryoprobe 200.

Figure 3:
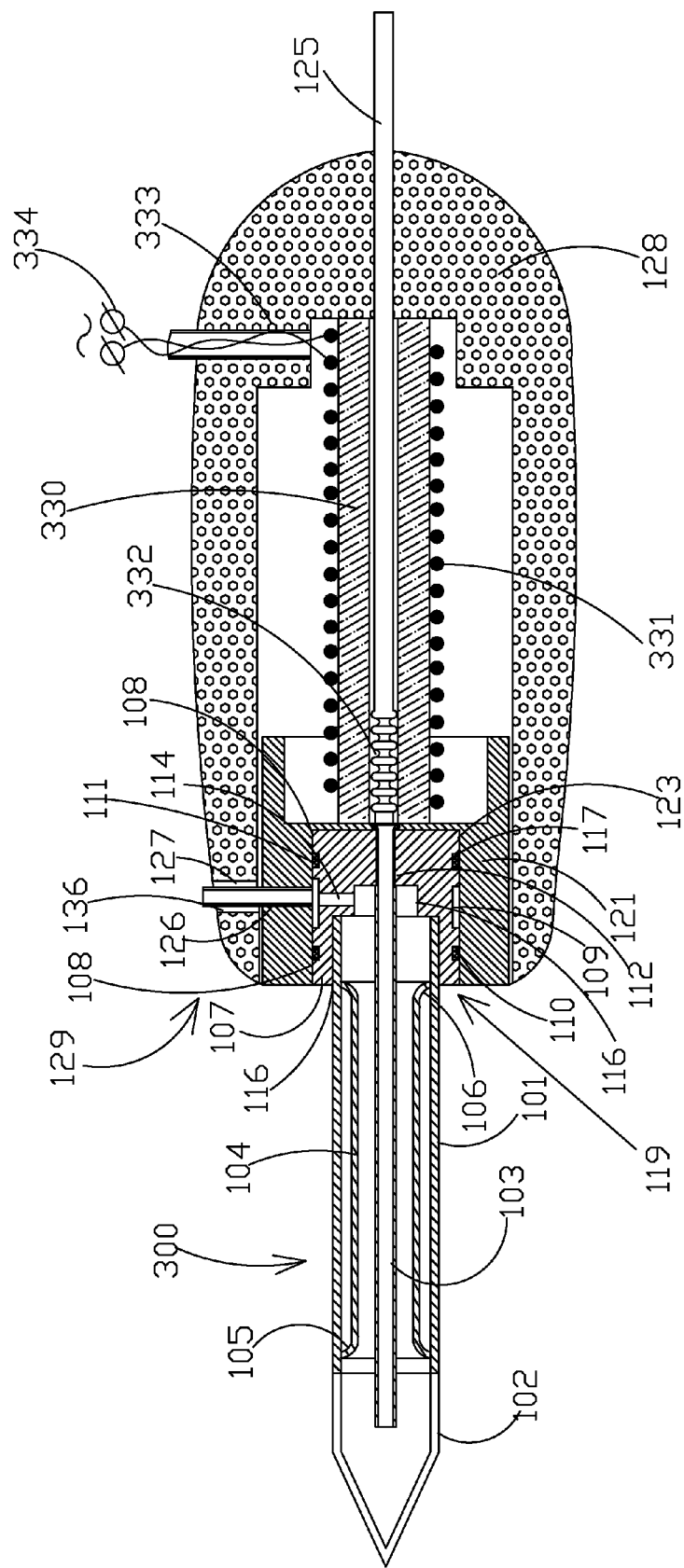
FIG. 3 is an axial cross-section of an exemplary, non-limiting, illustrative cryoprobe with a built-in vibrating electromagnetic mechanism constructed as a magnetostrictor, consistent with at least one embodiment of the present invention.

Referring now to FIG. 3, there is illustrated an axial cross-section of an exemplary, non-limiting, illustrative cryoprobe with a built-in vibrating electromagnetic mechanism constructed as a magnetostrictor, consistent with at least one embodiment of the present invention.

In FIG. 3, like numerals are used to identify like elements of cryoprobe 300 that have the same or similar function as the cryoprobe 100 of FIG. 1.

The distal section of cryogen supply tube 125 is preferably provided with a bellows 332 to provide a spring-actuated join between the central feeding pipe 103 and the cryogen supply tube 125.

A cylindrical magnetostrictor 330 is preferably positioned around the cryogen supply tube 125; the distal face plane of this cylindrical magnetostrictor 330 is in immediate contact with the female quick coupling unit 129. An electrical coil 331 is wound on the external surface of the cylindrical magnetostrictor 330; this electrical coil 331 is connected by wires 335, which are situated in a tubular piece 333 in handle 128, with external contacts 334. Periodic changing electrical current in the electrical coil 331 causes periodic extension and contraction of the cylindrical magnetostrictor 330 in the axial direction and, in turn, and with the same frequency, vibration of cryoprobe 300 in the axial direction. The frequency of vibration is preferably in the range of tens until hundreds Hz.

In operation, cryogen again preferably enters as described for cryoprobe 100 of FIG. 1. For the application of simultaneous axial vibrations, the electrical current in the electrical coil 331 is changed periodically; with the same period, the cylindrical magnetostrictor 330 expands and contracts in the axial direction, thereby causing vibrations having the same frequency in the axial direction of at least cryotip 102 and preferably cryoprobe 300.

Figure 4:
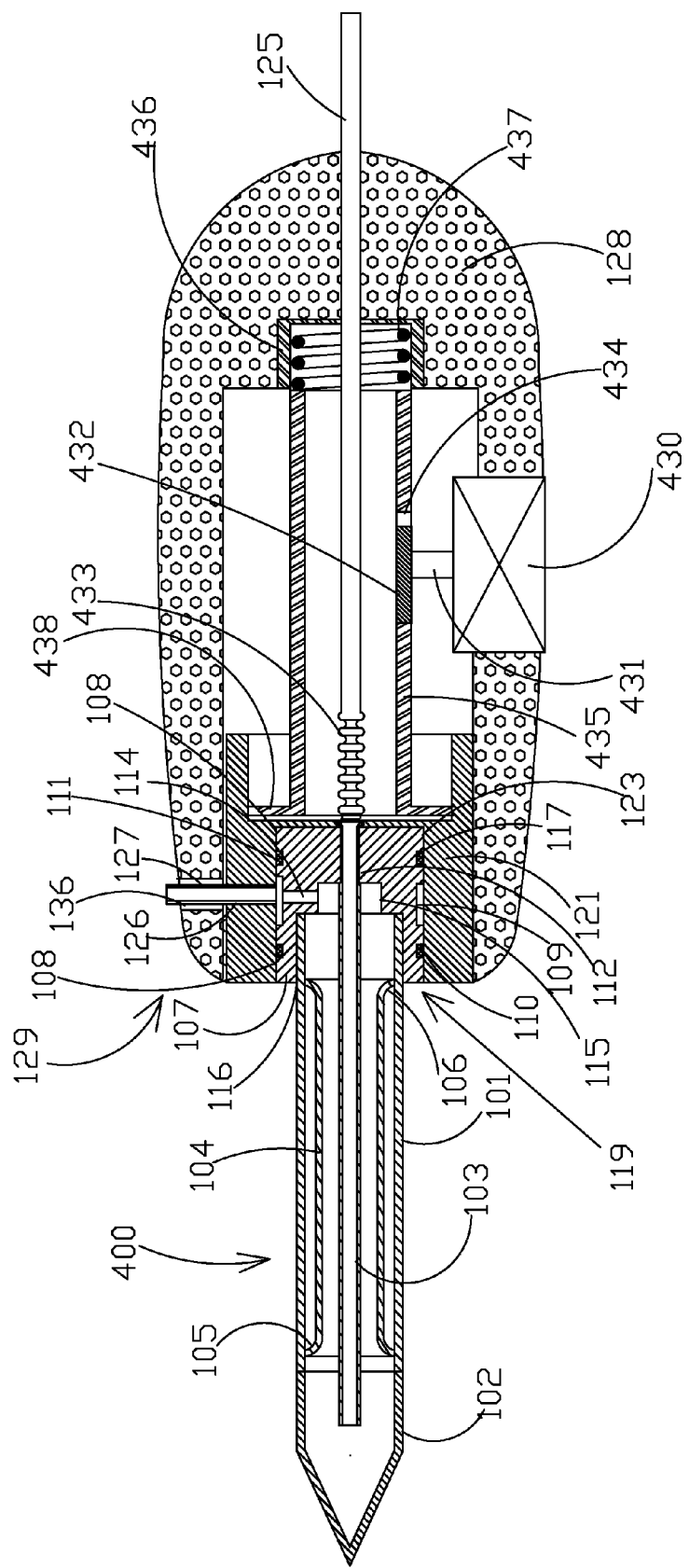
FIG. 4 is an axial cross-section of an exemplary, non-limiting, illustrative cryoprobe with a built-in vibrating mechanism actuated by a rotating eccentric gear, consistent with at least one embodiment of the present invention.

Referring now to FIG. 4, there is illustrated an axial cross-section of an exemplary, non-limiting, illustrative cryoprobe with its proximal male and female quick coupling units, a handle with a built-in vibrating mechanic mechanism actuated by a rotating eccentric, consistent with at least one embodiment of the present invention.

In FIG. 4, like numerals are used to identify like elements of cryoprobe 400 that have the same or similar function as the cryoprobe 100 of FIG. 1.

An electrical motor 430 is preferably located in handle 128. Electrical motor 430 rotates eccentric gear 432 installed on the electrical motor axle 431. Bushing 435 with a distal flanging 438 is installed in handle 128 concentrically with the cryogen supply tube 125. Bushing 435 is spring-actuated by helicoidal spring 437 installed in a proximal bushing 436. Bushing 435 is provided with an opening 434. Eccentric gear 432 during its rotation causes axial oscillating displacement of bushing 435 and, through the distal flanging 438, axial vibration of cryoprobe 400 itself. The distal section of cryogen supply tube 125 is provided with a bellows 433 to provide a spring-actuated join between the central feeding pipe 103 and the cryogen supply tube 125.

In operation, cryogen again preferably enters as described for cryoprobe 100 of FIG. 1. For the application of simultaneous axial vibrations, electrical motor 430 causes eccentric gear 432 to rotate, which in turn causes axial oscillating displacement of bushing 435 and, through the distal flanging 438, axial vibrations of at least cryotip 102 and preferably cryoprobe 400.

Aspects of the present invention also include cryotherapy methods.

Figure 5:
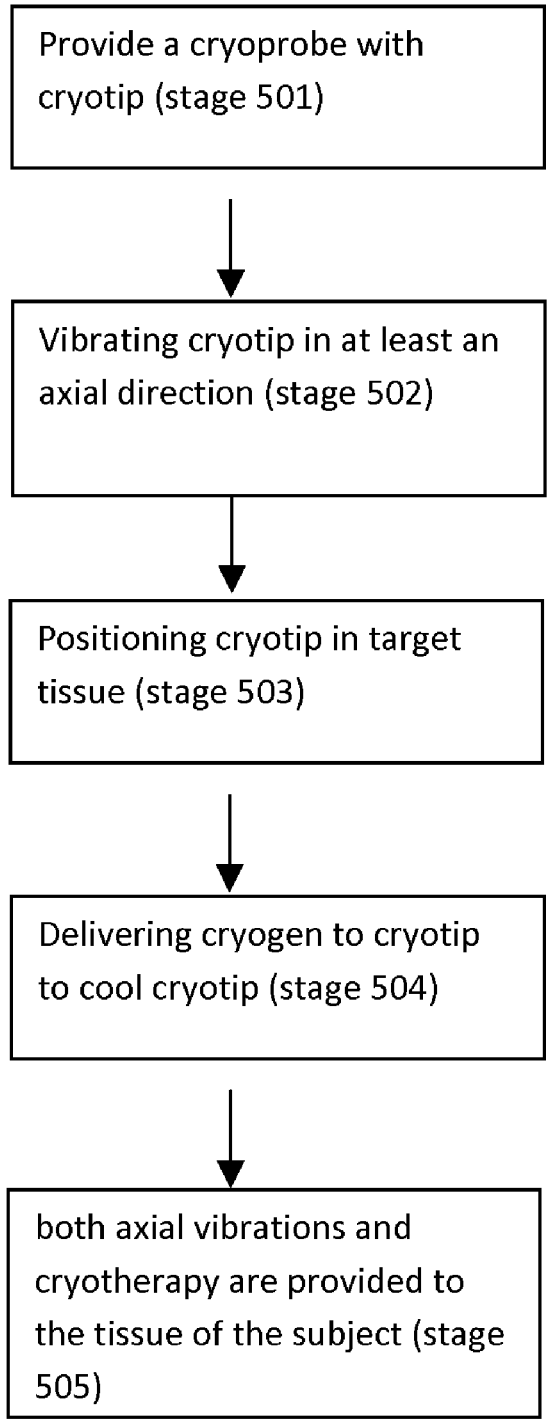
FIG. 5 is a flowchart of an exemplary, non-limiting, illustrative method consistent with at least one embodiment of the present invention for providing simultaneous vibrations and cryotherapy to a tissue of a subject.

Referring to FIG. 5, there is illustrated a flowchart of an exemplary, non-limiting, illustrative method 500 that is consistent with at least one embodiment of the present invention for providing simultaneous vibrations and cryotherapy to a tissue of a subject.

The method 500 includes the following operations: providing a cryoprobe with a cryotip (501); vibrating the cryotip (502); positioning the cryotip in a target tissue (503); cooling the cryotip by delivering cryogen to the cryotip (504); and providing therapeutic cryotherapy to the target tissue (505).

At least the cryotip, and preferably the entire cryoprobe, is axially vibrated by operation of a vibration section. In operation 505, preferably both axial vibrations and cryotherapy are provided simultaneously or substantially simultaneously to the tissue of the subject, optionally for an extended period of time, preferably at least until an ice ball having a desired diameter forms around the cryotip. Also, operations 502 through 504 need not be executed in the illustrated order. Indeed, in some applications, it is contemplated that the positioning may optionally occur during the vibrating. Further, the vibrating may optionally be only in the axial direction.

As can be seen from the foregoing, embodiments of the present invention provide cryosurgical probes that feature vibration in the axial direction. Further, the axial vibration of the cryosurgical probe may additionally and/or alternatively be actuated before operation in a freezing mode so to facilitate penetration of the probe into tissue. In addition, this vibration can be used to assist in the freezing-thawing operational cycle of the cryoprobe.

For example, various non-limiting embodiments according to the present invention of a mechanism causing vibration of a cryosurgical probe in its axial direction are described herein. One such embodiment optionally features application of a pneumatic cylinder constructed from two coaxial bellows; the distal face plane of this pneumatic cylinder is joined with a female member of a coupling unit of the cryosurgical probe. The pneumatic cylinder is actuated by an external source of a gaseous medium, preferably air, with alternating high and low pressure.

Another embodiment optionally features application of a flat bellows, which is situated in an immediate contact with the female unit. The pneumatic cylinder is actuated by an external source of a gaseous medium, preferably air, with alternating high and low pressure.

Yet another embodiment optionally features application of an electromagnetic vibrator, preferably in the form of a magnetostrictor. The magnetostrictor is constructed as a tubular piece from magnetostricting materials with a wire coil that is wound on its outer surface. The distal face plane of the magnetostrictor is joined with the female member of a coupling unit of the cryosurgical probe.

Still another embodiment optionally features application of a mechanical vibrator in the form of a motor with an eccentric gear that causes oscillating motion of a tubular piece with a slot; this tubular piece is preferably spring-actuated at its proximal end and is joined with the female member of a coupling unit of the cryosurgical probe.

Optionally a central feeding tube, which supplies a cryogen into the cryosurgical probe, can be provided with a bellows distal section ensuring tight contact between the central feeding tube and the central lumen of the cryosurgical probe. In another embodiment the distal section of the central feeding tube is preferably coiled thereby providing elasticity in the axial direction to the central feeding tube.

It is to be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

Although selected embodiments of the present invention have been shown and described, it is to be understood the present invention is not limited to the described embodiments. Instead, it is to be appreciated that changes may be made to these embodiments without departing from the principles and spirit of the invention, the scope of which is defined by the claims and the equivalents thereof.

What is claimed is:

1. A cryoprobe comprising:
a shaft having a central axis, a tip at a first end, a male socket section at a second end opposite the first end, a cryogen feeding pipe extending from the tip through the male socket section along the axis, and a cryogen return passage extending from the tip through the male socket section; and
a handle having a female socket adapted and configured to receive and connect with the male socket section in a quick connect manner, a vibration section that selectively causes vibration along the axis, a cryogen exhaust passage extending from the female socket to an exterior of the handle, and a cryogen supply tube connected to the female socket at an end of the tube,
wherein, when the male socket section is received by and connected with the female socket section, the cryogen exhaust passage is in communication with the cryogen return passage, the cryogen supply tube is in communication with the cryogen feeding pipe, and the vibration section selectively causes the male socket section to vibrate along the axis.

2. The cryoprobe of claim 1, wherein the cryogen supply tube comprises a flexible section at or near the end that permits a change in a length of the cryogen supply tube, and
wherein the length of the cryogen supply tube cyclically expands and contracts in the lengthwise direction during vibration of the vibration section.

3. The cryoprobe of claim 2, wherein the flexible section comprises a bellows.

4. The cryoprobe of claim 2, wherein the flexible section comprises a flexible helical coil.

5. The cryoprobe of claim 1, wherein the socket sections, the cryogen feeding pipe, and the cryogen supply tube are on the axis.

6. The cryoprobe of claim 1, wherein the vibration is only along a single axis.

7. The cryoprobe of claim 1, wherein the vibration section comprises a pair of concentric bellows with respective internal spaces and lengths that are responsive to changes in pressures in the internal spaces, and wherein changes in the lengths of bellows vibrates the female socket and, in turn, the tip.

8. The cryoprobe of claim 7, wherein the concentric bellows are independently responsive to changes in pressures.

9. The cryoprobe of claim 1, wherein the vibration section is comprises an expandable bladder that is concentrically disposed about the cryogen supply tube and has a volume that is responsive to changes in internal pressure, and wherein changes in the volume vibrates the female socket and, in turn, the tip.

10. The cryoprobe of claim 1, wherein the cryogen supply tube includes a helical coil at or near the end.

11. The cryoprobe of claim 1, wherein the vibration section is pneumatically responsive.

12. The cryoprobe of claim 1, wherein the vibration section is electromagnetically responsive.

13. The cryoprobe of claim 1, wherein the vibration section comprises a magnetorestrictor with a length that changes in response to changes in a supplied current, and wherein changes in length of the magnetorestrictor vibrates the female socket and, in turn, the tip.

14. The cryoprobe of claim 13, wherein the magnetorestrictor is cylindrical and surrounds the cryogen supply tube.

15. The cryoprobe of claim 1, wherein the vibration section comprises an electric motor that rotates an cam in mechanical communication with a bushing, and wherein rotation of the cam moves the bushing cyclically, which vibrates the female socket and, in turn, the tip.

16. A cryoprobe comprising:
a rigid shaft having a tip at a distal end, a male socket section at a proximal end, inner and outer passages extending from the tip through the male socket section; and
a body having a female socket section that connects with the male socket section, a vibration section that selectively causes axial vibration, a cryogen exhaust passage extending from the female socket to ambient, and a cryogen supply tube connected to the female socket,
wherein, when the male and female socket sections are connected, the cryogen exhaust passage is in communication with the outer passage, the cryogen supply tube is in communication with the inner passage, and the vibration section selectively causes the male socket section to vibrate axially.

17. A cryotherapy method, comprising:
vibrating a cryotip of a cryoprobe in an axial direction;
positioning the cryotip in a target tissue; and
cooling the cryotip,
wherein the cryprobe is the cryoprobe of claim 1.

18. The method of claim 17, wherein the positioning occurs during the vibrating.

19. The method of claim 17, wherein the vibrating is in only the axial direction due to the arrangement and configuration of the cryoprobe.

* * * * *